United States Patent
Doser et al.

(10) Patent No.: US 11,678,044 B2
(45) Date of Patent: Jun. 13, 2023

(54) APPARATUS AND METHOD FOR PROCESSING AN IMAGE DATA STREAM BY COMPARING FIRST AND SECOND CHECKING DATA STREAMS

(71) Applicant: Scholly Fiberoptic GmbH, Denzlingen (DE)

(72) Inventors: Ingo Doser, Villingen-Schwenningen (DE); Rainer Zwing, Villingen-Schwenningen (DE); Mohammed Shameem Hussain, Villingen-Schwenningen (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 434 days.

(21) Appl. No.: 16/840,606

(22) Filed: Apr. 6, 2020

(65) Prior Publication Data

US 2020/0322516 A1    Oct. 8, 2020

(30) Foreign Application Priority Data

Apr. 8, 2019   (DE) .......................... 102019109189.6

(51) Int. Cl.
*H04N 5/232* (2006.01)
*G06F 9/38* (2018.01)
(Continued)

(52) U.S. Cl.
CPC ........... *H04N 5/232* (2013.01); *G06F 9/3802* (2013.01); *G06F 9/3836* (2013.01); *G06T 1/20* (2013.01);
(Continued)

(58) Field of Classification Search
CPC .......... H04N 5/232; H04N 2005/2255; H04N 5/268; H04N 5/202; H04N 5/23229; H04N 9/04515; G06F 9/3802; G06F 9/3836; G06T 1/20; G06T 7/0002; G06T 2207/10068; G06T 2207/30168; H04L 65/60; H04L 65/61; A61B 1/045; A61B 1/00057; A61B 1/00011
See application file for complete search history.

(56) References Cited

U.S. PATENT DOCUMENTS

| 8,933,934 B1 | 1/2015 | Hill et al. |
| 2008/0018734 A1* | 1/2008 | Iriyama .................. A61B 1/045 348/72 |

(Continued)

*Primary Examiner* — Gevell V Selby
(74) *Attorney, Agent, or Firm* — Volpe Koenig

(57) ABSTRACT

A camera controller (1) with an image data stream input (2) and an image data stream output (4), wherein a first image data stream path (3) and a second image data stream path (5) are formed. An image processing unit (6) is arranged in the second image data stream path (5). A switching unit (7) is controlled by a comparison unit (8). The comparison unit (8) compares a first checking data stream (9), which was diverted from an image data stream (1) upstream of the image processing unit (6), and a second checking data stream (10), which was diverted from the image data stream downstream of the image processing unit (6). The image data stream paths are switched via the switching unit (7) if the deviation of the second checking data stream (9) from the first checking data stream (10) exceeds a threshold value.

16 Claims, 4 Drawing Sheets

(51) Int. Cl.
  *H04L 65/60* (2022.01)
  *H04L 65/61* (2022.01)
  *G06T 7/00* (2017.01)
  *G06T 1/20* (2006.01)
  *H04N 5/225* (2006.01)

(52) U.S. Cl.
  CPC ............ *G06T 7/0002* (2013.01); *H04L 65/60* (2013.01); *H04L 65/61* (2022.05); *G06T 2207/10068* (2013.01); *G06T 2207/30168* (2013.01); *H04N 2005/2255* (2013.01)

(56) References Cited

U.S. PATENT DOCUMENTS

| | | | |
|---|---|---|---|
| 2009/0324074 A1* | 12/2009 | Dembo | H04N 5/20 382/168 |
| 2014/0085324 A1 | 3/2014 | Charvet et al. | |
| 2017/0128031 A1* | 5/2017 | Vandenberghe | H04N 5/77 |
| 2018/0091740 A1* | 3/2018 | Hasegawa | H04N 5/23222 |

\* cited by examiner

APPARATUS AND METHOD FOR PROCESSING AN IMAGE DATA STREAM BY COMPARING FIRST AND SECOND CHECKING DATA STREAMS

INCORPORATION BY REFERENCE

The following documents are incorporated herein by reference as if fully set forth: German Patent Application No. 10 2019 109 189.6, filed Apr. 8, 2019.

TECHNICAL FIELD

A method and apparatus for image processing, in particular in a camera controller, having an image data stream input, which is connectable to the image output of an image recording apparatus, an image data stream output, which is connectable to an image display apparatus, a first image data stream path from the image data stream input to the image data stream output, and a second image data stream path from the image data stream input to the image data stream output, in which an image processing unit is arranged.

BACKGROUND

It is known, in particular in endoscopy, to prepare image data streams. There is here a desire for increasingly more complex preparation algorithms, for example for feature detection, to highlight specific image contents by color, or to measure the features and superpose the dimensions in the image data stream, or for general image improvement, such as for enhancing contrast.

It is known to use a graphic processor unit, GPU, to this end so as to be able to image these complex processing algorithms.

However, this gives rise to the problem that a sufficient failure safety must be ensured. In particular in endoscopic applications during a surgery, tearing or failure of the image data stream must be avoided under all circumstances.

To this end, the prior art has proposed to monitor the GPU with the aid of a monitoring module and, if the proper function of the GPU can no longer be ascertained, to bridge the image data stream path of the GPU.

To ascertain the correct function of the GPU, an additional monitoring unit that monitors critical parameters such as temperature and/or clock frequency can be present.

For monitoring, it is also possible for example to transmit an additional task to the GPU that the GPU must additionally work through so that, if the result of this additional task is not produced, it is possible to ascertain that the GPU no longer operates properly.

One problem is here that the GPU must reduce its output if it overheats and thus less computing capacity for the actual image processing is available.

SUMMARY

It is now an object of the invention to provide a method and an apparatus that provide a simple, fast and reliable detection of the correct function of an image processing unit.

This object is achieved by a method with one or more features of the invention.

The method according to the invention accordingly makes provision for a first checking data stream to be produced, for a second checking data stream to be diverted from the image data stream in the second image data stream path, for a deviation between the second checking data stream and the first checking data stream to be ascertained, and for the image data stream path to be switched over in dependence on the deviation.

Producing a checking data stream can take place outside the image processing unit (GPU), which is why no computing power of the GPU for processing additional tasks is necessary. A power reduction due to overheating accordingly does not occur, ensuring uninterrupted image processing. On the other hand, a malfunction can also be recognized very quickly and independently of the image processing unit, with the result that if the GPU fails or in the case of an error of the GPU, fast and reliable switching-off or bypassing can take place.

The checking data stream can practically be any piece of information that is associated or may be associated with the image data, for example a time signal or a timecode.

In an advantageous embodiment of the invention, the first checking data stream is diverted from an image data stream upstream of the image processing unit.

The idea is here to divert a first checking data stream practically directly from the input image data stream. The second checking data stream is diverted downstream of the image processing unit. If the image processing unit functions without error, both checking data streams should be identical or at least similar. In the reverse, a greater deviation between the two checking data streams signifies a malfunction of the image processing unit.

In an advantageous embodiment, a switch to the first image data stream path occurs if the deviation exceeds a threshold value. This threshold value can be fixedly specified or be variably dependent on other parameters. The first image data stream path bypasses the image processing unit, which is why in the case of a failure or malfunction of this unit at least one raw signal or a rudimentarily processed image data stream is present at the image data stream output. Consequently, an image data stream for representation on an image display apparatus is available almost without interruption.

In an advantageous embodiment, the second checking data stream is ascertained in the same way as the first checking data stream. In this way, the two checking data streams can be simply compared to one another and differences can be ascertained.

The two checking data streams can be diverted for example directly from the respective image data stream path and be compared.

Due to the possibly different signal propagation times in the second image data stream path, however, it may be advantageous if the first checking data stream is stored in a buffer. The second checking data stream is here compared to the stored first checking data stream.

In an advantageous embodiment, the buffer is embodied in the form of a FIFO memory. The latter permits in a simple manner a comparison of the temporal order, for example, of timestamps.

In a particularly advantageous embodiment of the invention, the first checking data stream is stored outside the visible image information in the image data stream. In this way, a simple temporal assignment of the checking data can take place.

The checking data stream can in particular be saved in a blanking interval, preferably in the vertical blanking interval. It can also be saved in the pixel data of a covered region and/or inactive region of the image sensor. In this way, a negative impact on the image data stream is ruled out.

In an advantageous embodiment of the invention, the checking data from the first checking data stream stored in the image data stream are extracted from the image data stream downstream of the image processing unit as a second checking data stream and compared to the checking data, which are stored in the buffer, of the first checking data stream. In this way, it is particularly simple to ascertain a deviation between the two checking data streams.

In an expedient embodiment, the first checking data stream is a sequence of timestamps that are assigned to the individual images of the image data stream. The deviation is here ascertained from the order and temporal deviation of the timestamps in the second checking data stream. The timestamps are to this end saved not only in the buffer, but also in the image data stream. If the image processing unit is defective, the timestamp in the image signal is changed, falsified or removed. That means the second checking data stream is changed. A comparison of the second checking data stream to the first checking data stream in the buffer thus permits fast and unique detection of a fault or a defect of the image processing unit.

In one development of the invention, in the image processing unit, the timestamp is extracted at the beginning of each partial processing step and added again to the processed image at the end of the partial processing step. In this way, it is not only possible to detect a defect or an error of the image processing unit, but it is also possible to detect individual faulty processing steps. To this end, it may be advantageous if the second checking data stream is compared to the first checking data stream after every processing step. In this way, it is possible even before the image processing is complete to detect a defect or an error and for a switch to the first image data stream path to be triggered. The switch accordingly takes place even faster, such that any image failure is shorter or does not occur at all.

In an alternative embodiment of the invention, the first checking data stream is a temporal profile of a brightness, of a histogram or of other image information of the image data stream. It has been shown that, even though such checking data streams change due to the image processing, basic properties, such as for example the temporal position of maxima and minima are maintained. To compare such checking data streams, it is therefore possible to calculate for example a correlation of the two checking data streams.

Generally, a camera controller has an image control unit or a rudimentary image processing unit, which prepares the raw data of an image sensor such that they can be guided to an image display apparatus. This image control unit or generally the image processing units of the first image data stream path generally have a design that is as simple and cost-effective as possible.

In an advantageous embodiment of the invention, the second image data stream path is diverted from the first image data stream path upstream of such an image control unit of the camera controller. This prevents negative image influences on account of these simple image signal processing units from also being contained in the second image data stream and from no longer being removable there.

The invention also comprises a camera controller, having an image data stream input, which is connectable to the image output of an image recording apparatus, an image data stream output, which is connectable to an image display apparatus, a first image data stream path from the image data stream input to the image data stream output, a second image data stream path from the image data stream input to the image data stream output, in which an image processing unit is arranged, a switching unit with which an image data stream is switchable between the first image data stream path and the second image data stream path. This camera controller is characterized according to the invention in that the camera controller has a comparison unit programmed as part of the controller, which is connected to the switching unit and which can compare a first checking data stream and a second checking data stream, which was diverted from the image data stream downstream of the image processing unit, and which can transmit a switching signal to the switching unit such that a switch to the first image data stream path occurs if the deviation of the second checking data stream from the first checking data stream exceeds a threshold value.

In particular, the first checking data stream can have been diverted from the image data stream upstream of the image processing unit.

The camera controller preferably has a buffer, in particular a FIFO memory, for storing the first checking data stream. Such a buffer simplifies the comparison of the checking data streams even in the case of different propagation times of the two image data stream paths.

In particular, the camera controller is embodied and/or set up for performing the method according to the invention.

The invention furthermore comprises a camera system, in particular a video endoscope, with a camera controller according to the invention, with at least one image recording apparatus, with an objective lens, and with an image sensor, which is connected to the image data stream input of the camera controller, and with at least one image display apparatus, which is connected to the image data stream output of the camera controller.

BRIEF DESCRIPTION OF THE DRAWINGS

The invention will be explained in more detail below on the basis of a few advantageous exemplary embodiments with reference to the attached drawings, in which.

DETAILED DESCRIPTION

Figure 2:
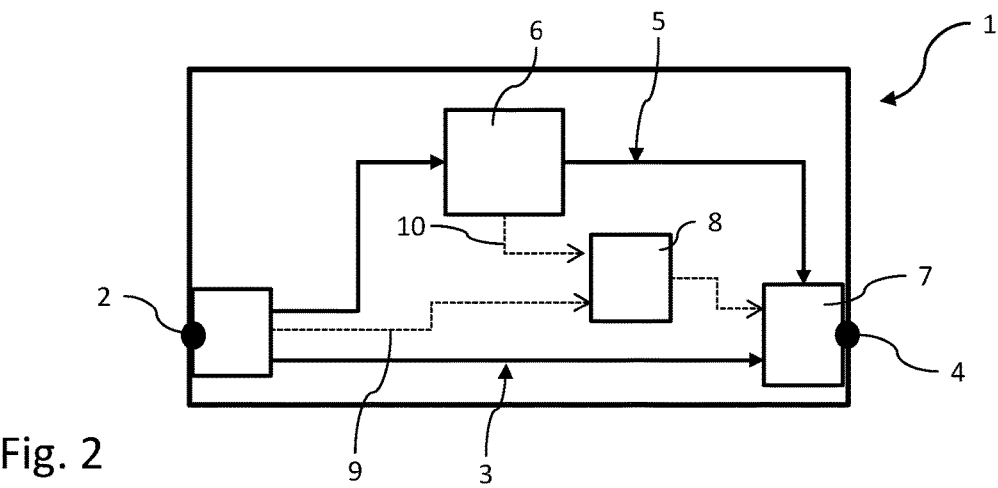
FIG. 2: shows a block diagram of a camera controller according to the invention.

FIG. 2 shows a block diagram of a camera controller according to the invention, which is denoted overall with 1.

The camera controller 1 has an image data stream input 2, which can be connected for example to a video camera or to a camera head of an endoscope. The image data stream input 2 can receive for example an image data stream of an image sensor.

The image data stream input 2 is connected, via a first image data stream path 3, to an image data stream output 4. The image data stream output 4 is connectable for example to an image display apparatus, such as a display screen.

The camera controller 1 has a second image data stream path 5, which connects the image data stream input 2 to the image data stream output 4. However, an image processing unit 6 is arranged in the second image data stream path 5.

This image processing unit 6 can have, for example, a graphic processor or a special image signal processor or a combination of different processors. Using the image processing unit 6, complex image processing tasks are able to be performed, for example feature detection, image improvement and superposition of further information.

In the standard setting, the second image data stream path 5 and thus the image processing unit 6 are active. According to the invention, a switch to the first image data stream path 3 now takes place if the image processing unit 6 is defective or if no image data stream is present, or only a defective image data stream is present, at the image data stream output 4 for a different reason.

To this end, in the example, the image data stream output 4 has a switching unit 7, which is controlled by a comparison unit 8. The comparison unit 8 receives a first checking data stream 9, which is diverted in the example in the image data stream input 3, and a second checking data stream 10, which is diverted in the image processing unit 6. In the comparison unit 8, the two checking data streams are compared and the deviation is ascertained.

The switch to the first image data stream path 3 is effected in accordance with a method according to the invention if the deviation exceeds a threshold.

Figure 1:
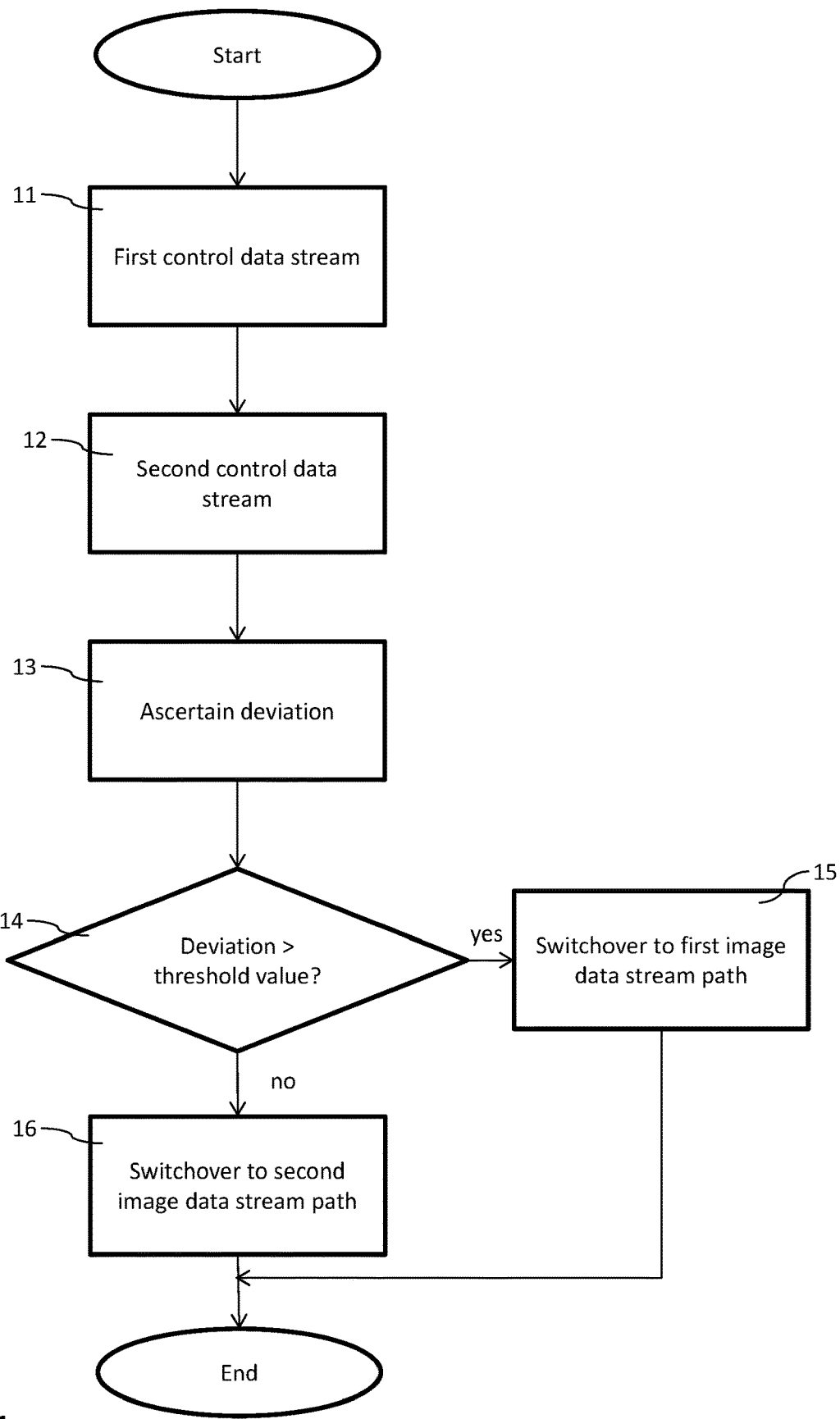
FIG. 1: shows a flow chart of a performance of the method according to the invention.

FIG. 1 shows a flow chart of an advantageous embodiment of a method according to the invention.

In a first step 11, a first checking data stream 9 is diverted from the image data stream. This can take place in the first image data stream path 3 or in the second image data stream path 5. At any rate, the diverting takes place upstream of the image processing unit 6. The first checking data stream 9 can for example be a sequence of timestamps or a temporal brightness profile or another piece of information associated with the image data stream.

In a second step 12, a second checking data stream 10 is diverted downstream of the image processing unit 6 in the second image data stream path 5. The second checking data stream 10 is preferably diverted in the same way as the first checking data stream 9.

In the subsequent step 13, a deviation between the second checking data stream 10 and the first checking data stream 9 is ascertained. Depending on the type of the checking data streams, the deviation can be ascertained for example as the temporal deviation of timestamps, an incorrect order of the timestamps, or a deviating brightness distribution. It is also possible for example to ascertain a correlation of the checking data streams if a simple comparison is not possible.

In the subsequent step 14, the ascertained deviation is compared to a threshold value. If the ascertained deviation is greater than the threshold value, then, in a switching step 15, for example using a switching unit 7, a switch to the first image data stream 3 is performed and thus a defective image processing unit 6 is bridged or bypassed. If the deviation is below the threshold value, the second image data stream path 5 is switched on 16 or maintained. The method is then repeated cyclically.

The method is a continuous method, which begins with the switching-on of the camera controller 1 and ends only upon switch-off. The method can moreover be synchronized with the image data stream input 2, such that, for example, a new cycle begins in each case after a complete image is received.

Figure 3:
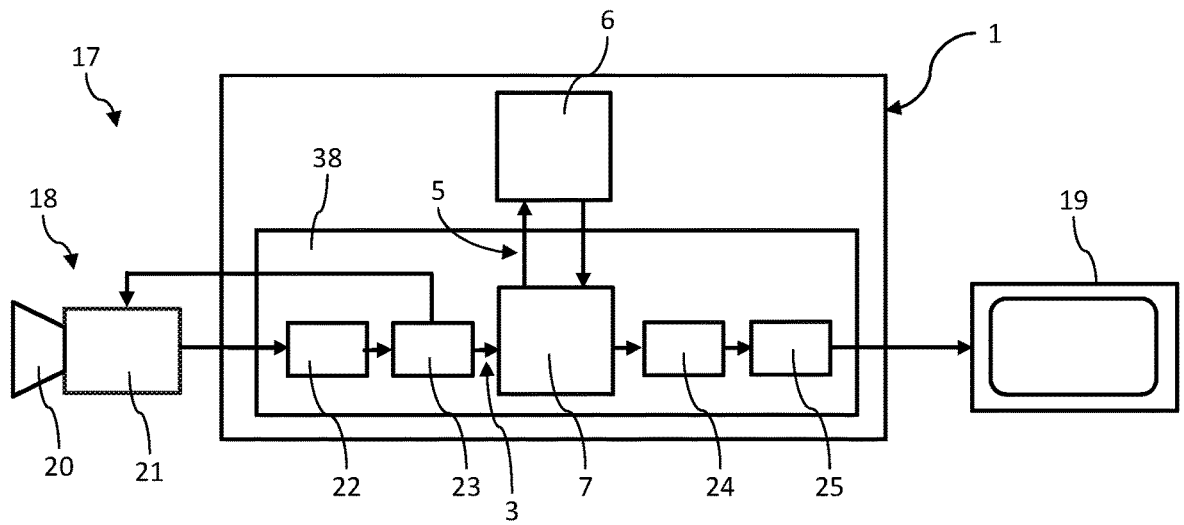
FIG. 3: shows a block diagram of a camera system according to a first embodiment of the invention.

FIG. 3 shows a camera system 17 in accordance with a first embodiment of the invention. The camera system has a camera controller 1, an image recording apparatus 18, and an image display apparatus 19.

The image recording apparatus 18 has an objective lens 20 and an image sensor 21, which is connected to the image data stream input 2 of the camera controller. The image display apparatus 19 is connected to the image data stream output 4 of the camera controller 1.

The camera controller 1 in this embodiment has an image processing unit 39 in the first image data stream path 3. The image processing unit 39 has a decoder unit 22 for preparing the image data of the image sensor 21. Downstream of the decoder unit 22, a camera control unit 23 is connected, which is connected, via a camera control line 24, to the image recording apparatus 18 so as to control camera parameters such as exposure or the f-number. The camera control unit 23 also performs image-sensor-specific adaptations, such as gamma correction or de-Bayering. Downstream of the camera control unit 23, a switching unit 7 is connected, which here implicitly also has a comparison unit 8 in accordance with FIG. 2, which receives and compares checking data streams.

Due to the switching unit 7, a switch to a second image data stream path 5 can be performed, in which an image processing unit 6 for complex image processing is arranged. The second image data stream path 5 is also led back in the switching unit. The downstream screen adaptation unit 24 regulates for example brightness, contrast and image sharpness of the image. Finally, the image processing unit 39 has an encoder unit 25, which adapts the image signal to conventional interfaces such as HDMI, DisplayPort or SDI. The encoder unit 25 is connected to the image data stream output 4. The image processing unit 39 is preferably embodied as a logic module, in particular as an FPGA, wherein all units contained are contained in the logic module.

Figure 4:
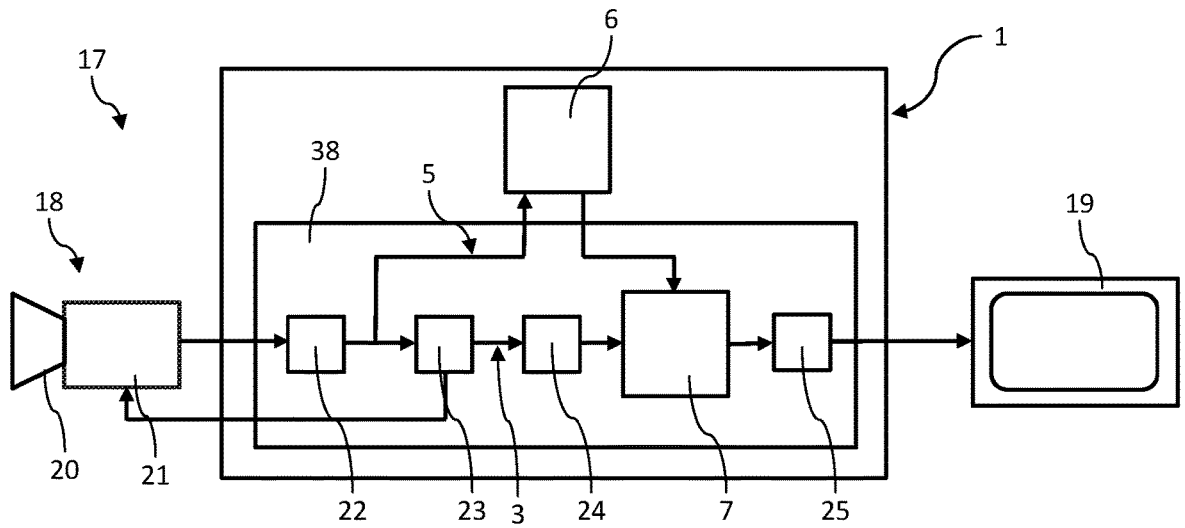
FIG. 4: shows a block diagram of a camera system according to a second embodiment of the invention.

FIG. 4 shows a camera system 17 having a camera controller 1, which substantially corresponds to the camera controller of FIG. 3. However, in this embodiment, the second image data stream path 5 already diverts after the decoder unit 22. The components arranged in the first image data stream path 3, in particular the camera control unit 23, contains only rudimentary image processing functions for cost reasons. For this reason, losses in terms of image quality and other image artifacts may occur here. Due to the previous diverting of the second image data stream path 5, it is avoided that these image errors are also contained in the image data stream, which was prepared with much outlay, of the image processing unit 6 and can no longer be removed therefrom. The switching unit 7 in this embodiment is not arranged until after the screen adaptation unit 24.

Figure 5:
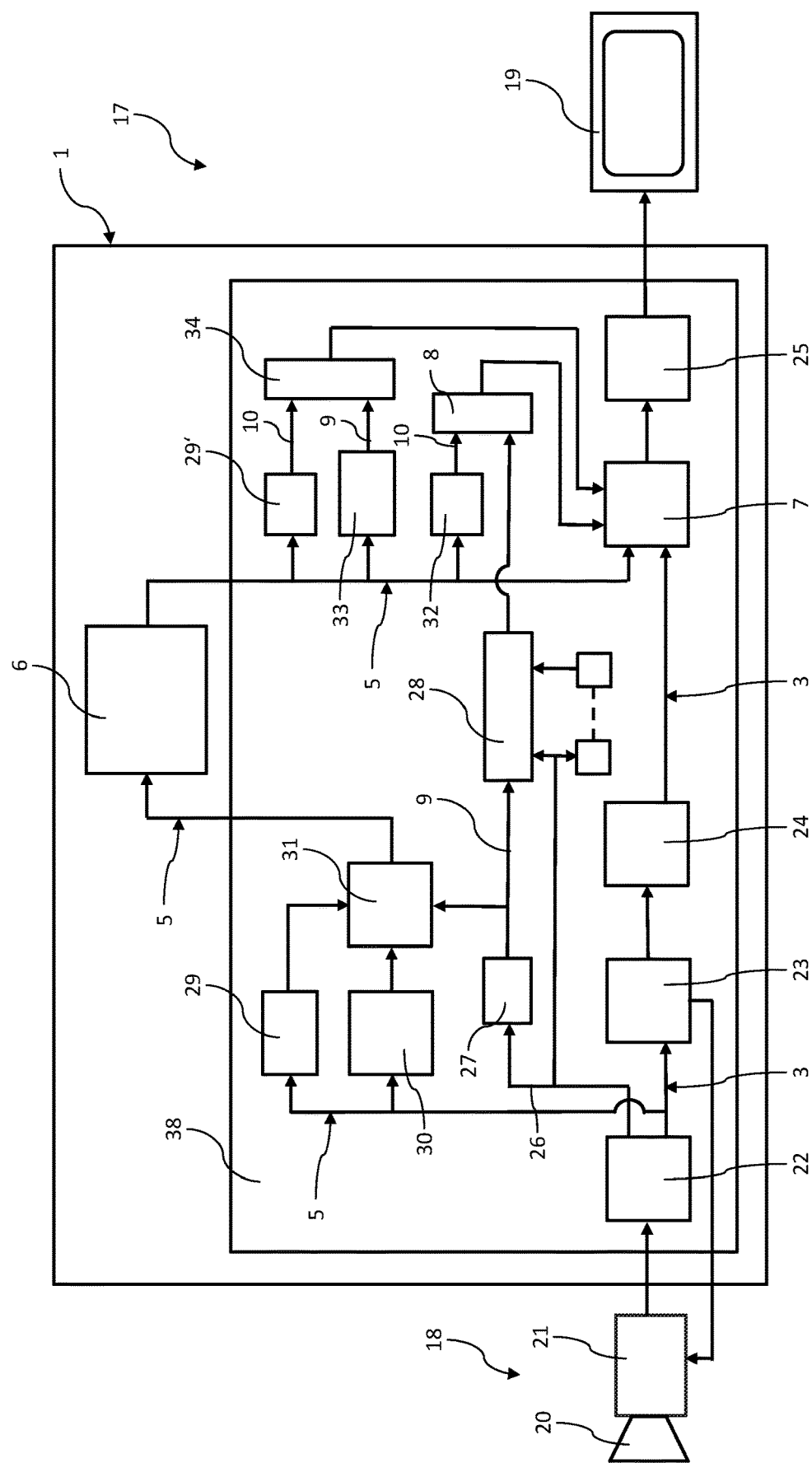
FIG. 5: shows a block diagram of a camera system according to a third embodiment of the invention.

FIG. 5 shows a camera system 17 having a further embodiment of a camera controller 1. This camera controller 1 corresponds in the first image data stream path to the camera controller 1 of FIG. 3. The second image data stream path 5 is diverted downstream of the decoder unit 22 in this embodiment, too.

The decoder unit 22 supplies a VSync signal 26 to a timestamp generator 27. The timestamps are stored as a first checking data stream 9 in a FIFO memory module 28. Even in this embodiment, the image processing unit 39 is preferably embodied in the form of an FPGA, wherein in particular also the FIFO memory module 28 can be formed within the FPGA.

Figure 7:
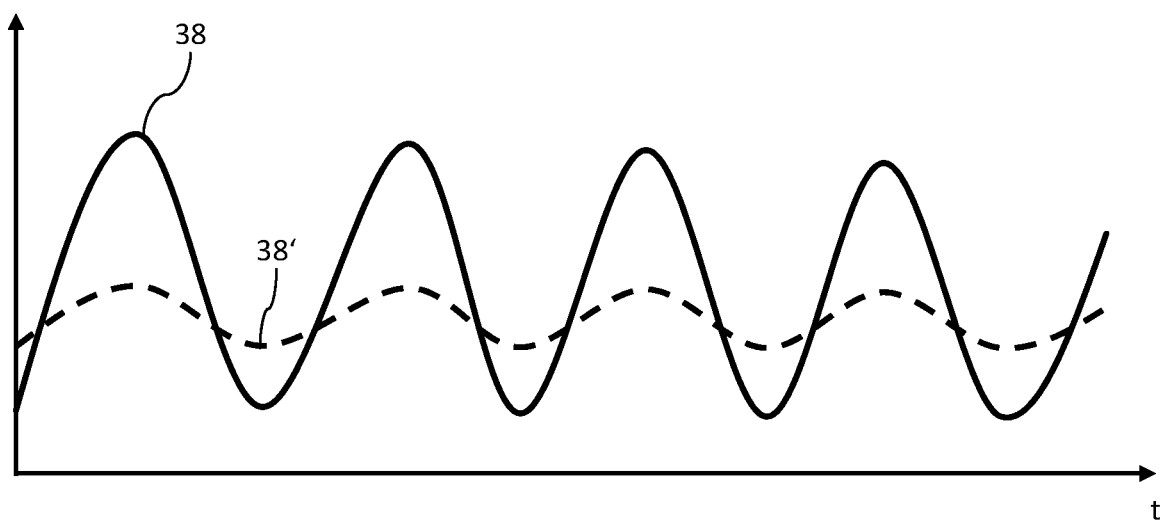
FIG. 7: shows a diagram of the brightness profiles of the image data stream before and after the image processing.

The embodiment shown additionally has a first video analysis unit 29, in which characteristic properties of the image data stream are ascertained, for example a brightness profile 38 (see FIG. 7). In a metadata unit 30, the image data stream is extended by a metadata region. This is typically done in a blanking interval of the image data stream or in the pixel data of an unused region of the image sensor. In a checking data unit 31, the video analysis is written as a further first checking data stream 9 of the video analysis unit 29 together with the appropriate timecode into the metadata region of the image data stream before the image data stream is passed to the image processing unit 6.

Downstream of the image processing unit 6, in a first extraction unit 32, the timestamp is extracted from the metadata region of the image data stream as a second checking data stream 10. In a comparison unit 8, which is connected to an output of the FIFO memory 28, said second checking data stream 10 is compared to the first checking data stream 9 from the FIFO memory 28 and a deviation is ascertained. The comparison unit 8 is connected to the switching unit 7 so as to perform a switch there if the deviation exceeds a threshold value.

In addition, the camera controller 1 shown has a second extraction unit 33, which extracts the video analysis data as a further first checking data stream from the metadata of the image data stream. A second video analysis unit 29' performs the same video analysis on the processed image data stream in parallel, which produces a further second checking data stream. In an analysis comparison unit 34, the two video analyses, i.e. checking data streams, are compared. The analysis comparison unit 34 is likewise connected to the switching unit 7, with the result that a switch can also be performed if the video analysis data deviate.

Figure 6:
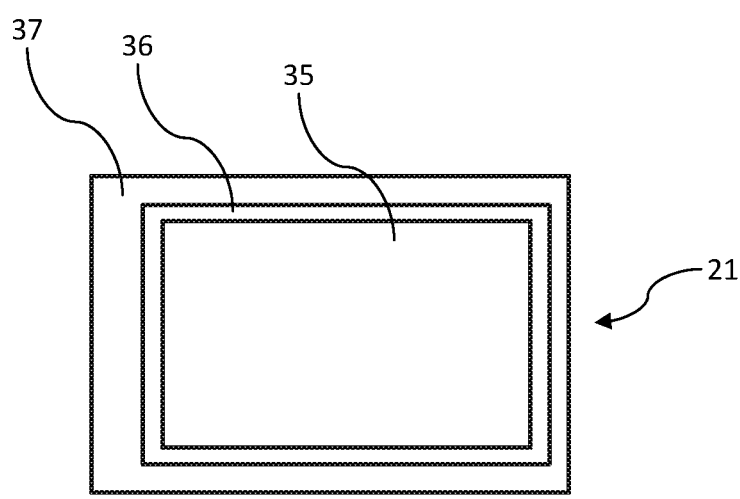
FIG. 6: shows a schematic illustration of an image sensor.

FIG. 6 shows by way of example an image sensor 21. The image sensor 21 has an active region 35, which is smaller than the area of the image sensor 21. Around the active region, there is a small passive region 36, which is illuminated but not used. Around said passive region 36, a covered region 37, which contains covered pixels, is present. This region is due to the time raster, which is the result of the pixel clock. The pixel clock produces more pixels per frame than the sensor has image points. The result of this is that not all the time raster rows and not all the image raster columns have active image points. The metadata of the image data stream can be saved for example in the pixel data of the covered region 37 and/or of the passive region 36, as a result of which the data capacity is significantly greater with respect to the blanking interval.

FIG. 7 shows by way of example a temporal brightness profile 38 of an image data stream, as is established for example by the first video analysis unit 29. The dashed line represents the temporal brightness profile 38' of the processed image data stream, as is established for example by the second video analysis unit 29'. Due to the image processing unit 6, the amplitude of the brightness profile 38 has changed, but the minima and maxima are maintained temporally. In the case of a defective image processing unit 6, for example the temporal positions of the minima and maxima would change. A deviation that can be used for the switch in the switching device 7 can be ascertained from the phase position of the two brightness distributions.

LIST OF REFERENCE SIGNS

1 Camera system
2 Image data stream input
3 First image data stream path
4 Image data stream output
5 Second image data stream path
6 Image processing unit
7 Switching unit
8 Comparison unit
9 First checking data stream
10 Second checking data stream
11 Method step 1
12 Method step 2
13 Method step 3
14 Method step 4
15 Method step 5
16 Method step 6
17 Camera system
18 Image recording apparatus
19 Image display apparatus
20 Objective lens
21 Image sensor
22 Decoder unit
23 Camera control unit
24 Screen adaption unit
25 Encoder unit
26 VSync signal
27 Timecode generator
28 FIFO memory
29 First video analysis unit
29' Second video analysis unit
30 Metadata unit
31 Checking data unit
32 First extraction unit
33 Second extraction unit
34 Analysis comparison unit
35 Active region
36 Passive region
37 Covered region
38 Brightness profile
38' Brightness profile of the processed image data stream
39 Image processing unit

The invention claimed is:

1. A method for image processing, the method comprising:
providing a camera controller (1) having an image data stream input (2) which is connectable to an image recording apparatus (18), an image data stream output (4) which is connectable to an image display apparatus (19), a first image data stream path (3) from the image data stream input (2) to the image data stream output (4), and a second image data stream path (5) from the image data stream input (2) to the image data stream output (4), in which an image processing unit (6) is arranged;
producing a first checking data stream (9);
diverting a second checking data stream (10) from the image data stream in the second image data stream path (5);
ascertaining a deviation between the second checking data stream (10) and the first checking data stream; and
switching over the image data stream path in dependence on the deviation.

2. The method as claimed in claim 1, wherein the switching over to the first image data stream path (3) occurs if the deviation exceeds a threshold value (14).

3. The method as claimed in claim 1, wherein the first checking data stream (9) is diverted (11) from an image data stream upstream of the image processing unit (6).

4. The method as claimed in claim 1, wherein the second checking data stream (10) is ascertained in a same way as the first checking data stream (9).

5. The method as claimed in claim 1, further comprising storing the first checking data stream (9) in a buffer.

6. The method as claimed in claim 5, wherein the buffer is a FIFO memory (28).

7. The method as claimed in claim 5, wherein the first checking data stream (9) is stored outside from visible image information in the image data stream.

8. The method as claimed in claim 5, wherein the first checking data stream (9) is stored in at least one of a blanking interval, a vertical blanking interval, or a passive region (36) or a covered region (37) of an image sensor (21).

9. The method as claimed in claim 8, further comprising extracting the checking data from the first checking data stream (9) stored in the image data stream from the image data stream downstream of the image processing unit (6) as a second checking data stream (10) and comparing the second checking data stream (10) to the checking data, which are stored in the buffer, of the first checking data stream (9).

10. The method as claimed in claim 9, wherein the first checking data stream (9) comprises a sequence of timestamps that are assigned to the individual images of the image data stream and the deviation is ascertained from an order and temporal deviation of the timestamps in the second checking data stream.

11. The method as claimed in claim 10, wherein in the image processing unit the timestamp is extracted at a beginning of each partial processing step and added again to a processed image at an end of the partial processing step.

12. The method as claimed in claim 1, wherein the first checking data stream (9) is a temporal profile of a brightness (38), of a histogram or of other image information of the image data stream.

13. The method as claimed in claim 1, wherein the second image data stream path (5) is diverted from the first image data stream path (9) upstream of a camera control unit (23) of the camera controller (1).

14. A camera controller (1), comprising:
an image processing unit (6),
an image data stream input (2) which is connectable to the image output of an image recording apparatus (18),
an image data stream output (4) which is connectable to an image display apparatus (19),
a first image data stream path (3) from the image data stream input (2) to the image data stream output (4),
a second image data stream path (5) from the image data stream input (2) to the image data stream output (4), in which the image processing unit (6) is arranged,
a switching unit (7) with which an image data stream is switchable between the first image data stream path (3) and the second image data stream path (5),
a comparison unit (8) connected to the switching unit (7) configured to compare a first checking data stream (9) and a second checking data stream (10), which was diverted from the image data stream downstream of the image processing unit (6), and which can transmit a switching signal to the switching unit (7) such that a switch to the first image data stream path (3) occurs if a deviation of the second checking data stream (9) from the first checking data stream (10) exceeds a threshold value.

15. The camera controller (1) as claimed in claim 14, wherein the camera controller (1) has a buffer that is configured to store the first checking data stream (9).

16. A camera system (17) comprising the camera controller (1) as claimed in claim 14, at least one image recording apparatus (18), with an objective lens (20) and an image sensor (21), connected to the image data stream input (2) of the camera controller (2), and at least one image display apparatus (19) connected to the image data stream output (4) of the camera controller (1).

* * * * *